United States Patent [19]
Olcott

[11] Patent Number: 4,467,212
[45] Date of Patent: Aug. 21, 1984

[54] RADIOACTIVE SOURCE PIGTAIL INSPECTION APPARATUS AND METHOD

[76] Inventor: Donald J. Olcott, 1107 S. Walnut St., Burlington, Wash. 98233

[21] Appl. No.: 262,044

[22] Filed: May 11, 1981

[51] Int. Cl.³ .......................... H04N 7/18; G21F 5/02
[52] U.S. Cl. .............................. 250/497.1; 250/358.1; 358/106
[58] Field of Search .......................... 250/358.1, 497.1; 378/58, 59, 60, 61; 358/100; 356/106

[56] References Cited

U.S. PATENT DOCUMENTS

| | | | |
|---|---|---|---|
| 3,643,096 | 2/1972 | Jeffries, Jr. et al. | 250/497.1 X |
| 3,848,137 | 11/1974 | Ellis | 250/497.1 |
| 4,286,287 | 8/1981 | Williams | 358/100 |
| 4,314,157 | 2/1982 | Gaines | 250/497.1 |

Primary Examiner—Alfred E. Smith
Assistant Examiner—Richard E. Hanig
Attorney, Agent, or Firm—Seed and Berry

[57] ABSTRACT

Apparatus and a method for utilizing existing radiographic weld testing equipment for inspecting from a remote location the condition of a radioisotope-carrying pigtail.

6 Claims, 3 Drawing Figures

RADIOACTIVE SOURCE PIGTAIL INSPECTION APPARATUS AND METHOD

DESCRIPTION

Technical Field

This invention pertains to remotely manipulated exposure devices for handling radioisotopes and, in particular, methods and apparatus for inspecting the end of a pigtail used in radiography.

BACKGROUND ART

Radiographic inspection of welds for large structural members, such as pipes or large cylinders, is done with a specialized type of equipment consisting of a portable shielded storage or container exposure device which contains a flexible, short wire or "pigtail" containing the radioactive isotope or radioactive source. This radioactive source must be kept shielded at all times when personnel are in the vicinity to avoid harmful exposure to the radiation. The isotope is, therefore, initially mounted to the pigtail at a few isolated laboratories in the United States and stored under heavily shielded conditions. The pigtail then is shipped to the user's location and is again stored until it is ready to be placed into the exposure device, which has a hollow conduit to guide the pigtail to the object to be tested. A flexible wire cable which can be reciprocated from a remote distance, for example, 25-30 feet away, and behind suitable shielding is used to move the pigtail through the exposure device thence through the hollow conduit, and into the vicinity of the object to be radiographed.

The shipping container containing a pigtail, with its new radioactive isotope, is coupled to the exposure device; the cable is then pushed into the exposure device and screwed to the fresh isotope-carrying pigtail; then the hollow conduit is substituted for the shipping container.

When testing pipe welds, etc., the free end of the conduit is usually brought within the center of the cylinder or pipe to be inspected. Then, by pushing the cable through the exposure device the pigtail having the radioactive isotope are pushed through the conduit to the end of the conduit. Radiographic film is on the outside of the container in the area to be X-rayed. If desired, an additional shielding block can be placed above the isotope in the container to reduce scattering of the radioactivity. When the desired amount of radiation has been emitted to expose the film, the pigtail is withdrawn by the cable back into the exposure device until it is needed again.

During movement of the pigtail in the conduit, the pigtail becomes weakened and occasionally breaks. If the pigtail breaks outside the exposure device there is considerable danger of overexposure of personnel to radiation. Since the testing is frequently done in an operating plant of some kind, this risk of overexposure of personnel may cause the plant or a substantial part of the plant to be shut down until the broken pigtail can be placed in a shielded container.

Heretofore, inspection of the pigtail for wear or potential breakage has been done haphazardly, with perhaps the best known equipment being the use of a mirror, auxiliary lighting and a remotely positioned telescope located in a shielding viewing area. The resolution, necessity of lighting, and the handling of the mirror for this inspection have never been satisfactory. The equipment is cumbersome and awkward to position and use.

DISCLOSURE OF THE INVENTION

It is an object of this invention to provide a radioisotope-carrying pigtail inspection apparatus.

It is another object of this invention to provide a method and apparatus for accurately and safely inspecting the radioisotope-carrying pigtail at the user location.

Basically, these objects are obtained by an apparatus which can support and couple to the conduit of the exposure device with close proximity television cameras coupled to a television at a safe viewing spot. The method then employs the steps of coupling the free end of the exposure devices conduit to the pigtail inspection device of the present invention while the pigtail is shielded pushing the pigtail through the conduit into a transparent section of the pigtail inspection device, remotely viewing the condition of the pigtail, and withdrawing the pigtail back into the shielded exposure device. Preferably, the viewing is done with two television cameras positioned ninety degrees to one another so that both top and side elevation views are recorded.

As is apparent, the invention provides accurate and safe viewing of the entire pigtail area using equipment readily available to the user of the radiography inspection equipment. Thus very little additional cost is required and little time is needed, assuring that frequent and proper inspections will be maintained.

BEST MODE FOR CARRYING OUT THE INVENTION

Figure 1:
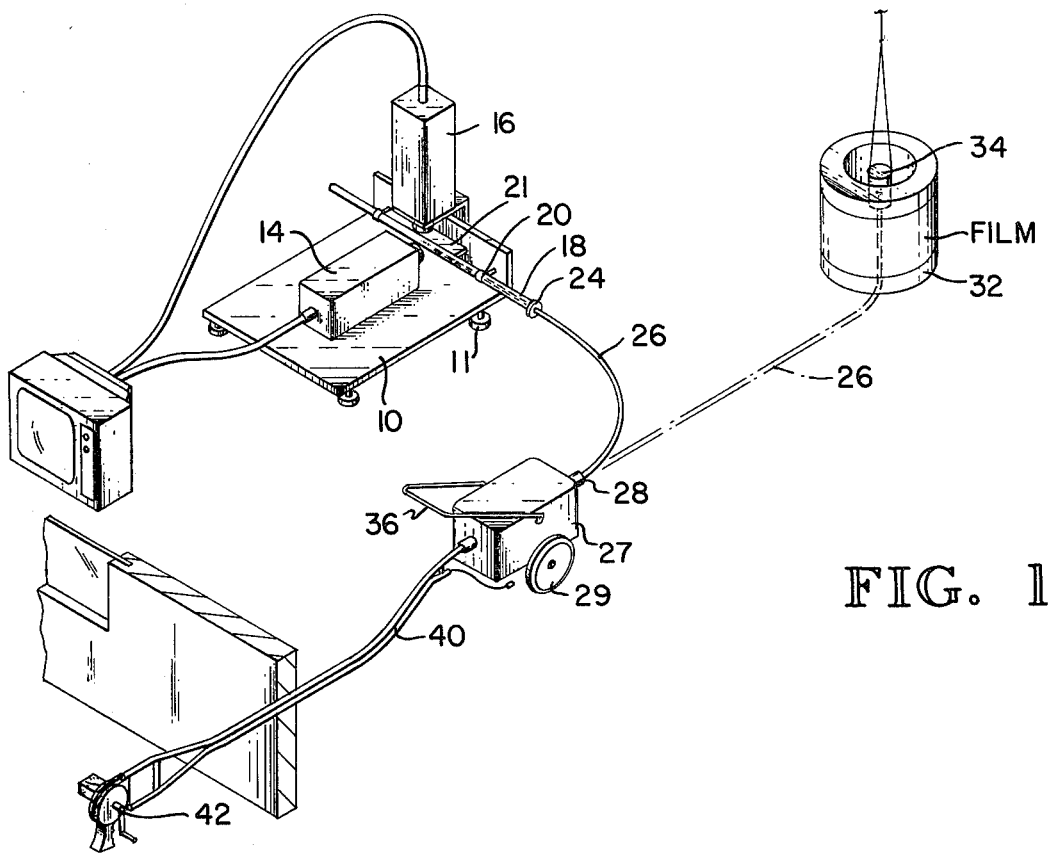
FIG. 1 is an isometric of an apparatus embodying the invention.

The pigtail inspecting apparatus includes a frame 10 with supporting legs 11. The frame supports a side elevation television camera 14 and a top plan television camera 16. Any commercial television camera, such as a Panasonic Model WV1300A, is suitable. The television cameras are positioned to view an elongated transparent support tube 18 which is fastened to the frame by a pair of rings 20 that are supported on bolts 21 adjustably coupled to the frame.

The end of the transparent viewing tube 18 is provided with a threaded coupling 24 of the type suitable to couple to the free end of a conduit 26 extending from the exposure device 27.

Figure 2:
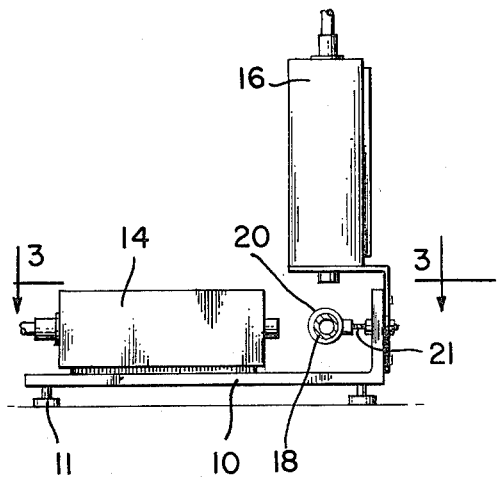
FIG. 2 is a schematic illustration of a typical radiography camera testing apparatus shown in conjunction with the pigtail inspection apparatus embodying the principles of this invention.
Figure 3:
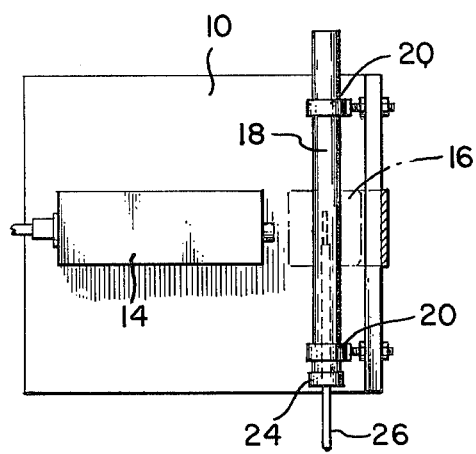
FIG. 3 is a top plan view of the apparatus of FIG. 2 taken along line 3—3 of FIG. 2.

The conduit 26, as best shown in FIG. 2, is coupled to the heavily shielded exposure device 27 at a coupling 28, which is also used for installing and removing pigtails directly from their shipping containers. The exposure device 27 is typically mounted on wheels 29 and has a handle 36 for positioning the device 27 at desired locations.

To radiograph the end of the conduit 26 is placed in the vicinity of the test object, such as a cylinder 32. Additional shielding 34 can be suspended above the radioactive source of the pigtail to reduce scattering since the radioactivity travels in all directions.

The pigtail is moved by an elongated flexible cable 40 which is coupled to the pigtail within the exposure device 27 from a remote location, such as at the handle 42. The handle 42 has a sprocket which engages spiral exterior of the cable 40 in a conventional manner to advance or withdraw the cable and the pigtail into and out of the device 27.

In the operation of the pigtail inspection apparatus, the pigtail is withdrawn into the device 27, the free end of the conduit 26 is coupled to the inspection tube 18 by threading the conduit to the coupling 24. Then, by advancing the pigtail from the remote location of handle 42, the cable moves the pigtail through the conduit 26 into the tube 18, where it can be viewed selectively by the television cameras.

A suitable viewing screen is coupled to the cameras for viewing the pigtail.

While the preferred embodiments of the invention have been illustrated and described, it should be understood that variations will be apparent to those skilled in the art without departing from the principle herein. Accordingly, the invention is not to be limited to the specific embodiment illustrated in the drawings.

I claim:

1. Apparatus for inspecting a radioisotope-carrying pigtail of the type used with standard object radiographic testing equipment having a shielded exposure device, a hollow conduit for guiding the pigtail from the device to the object to be examined, and means for moving the pigtail through the conduit into and out of the device, the improvement comprising:

a transparent inspection tube having an axis and a coupling for attaching the tube to the conduit for receiving said pigtail;

at least one camera mounted adjacent said inspection tube for viewing the pigtail in said inspection tube; and means operatively coupled to said camera for displaying the visual image of the pigtail within the tube.

2. The apparatus of claim 1 wherein said inspection tube is mounted on a frame, and wherein there are at least two cameras mounted on said frame at substantially right angles to one another and substantially perpendicular to the axis of the tube to allow viewing two orthogonal elevations of the pigtail.

3. A method of inspecting a radioisotope-carrying pigtail of the type used with standard object radiographic testing equipment having a shielded exposure device, a hollow conduit for guiding the pigtail from the device to the object to be examined, and means for moving the pigtail through the conduit into and out of the device, comprising the steps of:

coupling a free end of the conduit to an inspection tube;

moving the pigtail through the conduit into the inspection tube by means operable from a remote location;

viewing the pigtail while in the inspection tube by using television cameras to project images of the pigtail to a remote viewing location; and moving the pigtail back through the conduit into the shielded device.

4. An apparatus for safely inspecting a radioactive pigtail, comprising;

(a) an exposure device including a shielded container for holding the pigtail when the pigtail is not being used to radiograph;

(b) a conduit connected to the container;

(c) means for moving the pigtail in the conduit, the means being actuatable from a remote location;

(d) an inspection tube attached to the conduit, the tube having a longitudinal axis;

(e) at least two television cameras mounted orthogonal to each other and to the longitudinal axis of the tube; and (f) means operatively associated with the cameras for viewing the pigtail within the tube at the remote location.

5. The apparatus of claim 4 wherein the tube and cameras are mounted to a common frame.

6. An apparatus for safely inspecting a radioactive pigtail, comprising:

(a) a generally cylindrical, substantially transparent tube connectable to a conduit of the pigtail to allow close inspection of the pigtail at high resolution when the pigtail is extended into the tube, the tube having a longitudinal axis; and (b) at least two television cameras mounted orthogonal to each other and to the axis of the tube to allow viewing of the pigtail within the tube and to transmit the image of the pigtail to a remote location.

* * * * *